(12) United States Patent
Altwasser et al.

(10) Patent No.: US 8,859,459 B2
(45) Date of Patent: Oct. 14, 2014

(54) MULTILAYER CATALYST FOR PREPARING PHTHALIC ANHYDRIDE AND PROCESS FOR PREPARING PHTHALIC ANHYDRIDE

(75) Inventors: Stefan Altwasser, Wachenheim (DE); Jürgen Zühlke, Speyer (DE); Hans-Martin Allmann, Neunkirchen (DE); Frank Rosowski, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/173,736

(22) Filed: Jun. 30, 2011

(65) Prior Publication Data

US 2012/0004425 A1   Jan. 5, 2012

Related U.S. Application Data

(60) Provisional application No. 61/359,832, filed on Jun. 30, 2010.

(51) Int. Cl.
| | | |
|---|---|---|
| *B01J 23/04* | (2006.01) | |
| *B01J 27/186* | (2006.01) | |
| *B01J 35/00* | (2006.01) | |
| *C07D 307/89* | (2006.01) | |
| *B01J 27/198* | (2006.01) | |
| *B01J 21/06* | (2006.01) | |

(52) U.S. Cl.
CPC ............. *C07D 307/89* (2013.01); *B01J 27/186* (2013.01); *B01J 35/0006* (2013.01); *B01J 21/063* (2013.01); *B01J 35/0073* (2013.01); *B01J 27/198* (2013.01)
USPC .......................................... 502/344; 549/248

(58) Field of Classification Search
USPC ........................... 502/344, 242, 334; 549/248
See application file for complete search history.

(56) References Cited

U.S. PATENT DOCUMENTS

| | | | |
|---|---|---|---|
| 4,284,571 A | 8/1981 | Sato et al. | |
| 4,481,304 A | 11/1984 | Sato et al. | |
| 5,792,719 A | 8/1998 | Eberle et al. | |
| 5,969,160 A | 10/1999 | Lindstrom | |
| 6,288,273 B1 | 9/2001 | Heidemann et al. | |
| 6,362,345 B1 | 3/2002 | Heidemann et al. | |
| 6,528,683 B1 | 3/2003 | Heidemann et al. | |
| 6,586,361 B1 | 7/2003 | Heidemann et al. | |
| 6,700,000 B1 | 3/2004 | Heidemann et al. | |
| 7,371,893 B2 | 5/2008 | Storck et al. | |
| 2006/0276661 A1 | 12/2006 | Storck et al. | |
| 2007/0060758 A1 | 3/2007 | Storck et al. | |
| 2007/0135302 A1 | 6/2007 | Neto et al. | |
| 2009/0163726 A1 | 6/2009 | Wilmer et al. | |
| 2009/0286999 A1 | 11/2009 | Wilmer et al. | |
| 2009/0306409 A1 | 12/2009 | Guckel et al. | |
| 2009/0312562 A1 | 12/2009 | Guckel et al. | |
| 2009/0318712 A1 | 12/2009 | Wilmer et al. | |
| 2010/0069659 A1 | 3/2010 | Raichle et al. | |
| 2010/0069660 A1 | 3/2010 | Raichle et al. | |
| 2011/0028740 A1 | 2/2011 | Dobner et al. | |
| 2011/0034707 A1 | 2/2011 | Wilmer et al. | |
| 2011/0118487 A1 | 5/2011 | Abdallah et al. | |
| 2011/0124885 A1 | 5/2011 | Altwasser et al. | |
| 2011/0130273 A1 | 6/2011 | Karpov et al. | |
| 2011/0144387 A1 | 6/2011 | Wentink et al. | |
| 2011/0152433 A1 | 6/2011 | Bechtloff et al. | |
| 2011/0163278 A1 | 7/2011 | Domke et al. | |
| 2011/0195347 A1 | 8/2011 | Querner et al. | |
| 2011/0206753 A1 | 8/2011 | Karpov et al. | |
| 2011/0230668 A1 | 9/2011 | Altwasser et al. | |
| 2011/0245392 A1 | 10/2011 | Karpov et al. | |
| 2011/0250124 A1 | 10/2011 | Kramer et al. | |
| 2011/0251052 A1 | 10/2011 | Kramer et al. | |
| 2011/0251405 A1 | 10/2011 | Altwasser et al. | |
| 2011/0257413 A1 | 10/2011 | Dobner et al. | |
| 2011/0257414 A1 | 10/2011 | Dobner et al. | |
| 2012/0004425 A1 | 1/2012 | Altwasser et al. | |
| 2012/0043537 A1 | 2/2012 | Karpov et al. | |
| 2012/0071671 A1 | 3/2012 | Karpov et al. | |
| 2012/0077998 A1 | 3/2012 | Seeber et al. | |
| 2012/0086002 A1 | 4/2012 | Fleischhaker et al. | |
| 2012/0097068 A1 | 4/2012 | Riggs et al. | |
| 2012/0106139 A1 | 5/2012 | Ewald et al. | |
| 2012/0108713 A1 | 5/2012 | Ewald et al. | |
| 2012/0149919 A1 | 6/2012 | Altwasser et al. | |

FOREIGN PATENT DOCUMENTS

| | | |
|---|---|---|
| DE | 1269119 B | 5/1968 |
| DE | 2005969 A1 | 8/1971 |
| DE | 2948163 A1 | 6/1980 |
| DE | 40 06 935 A1 | 9/1991 |
| DE | 4109387 A1 | 9/1992 |
| DE | 19807018 A1 | 8/1998 |

(Continued)

OTHER PUBLICATIONS

U.S. Appl. No. 13/518,768.
Stanislaw E. Golunski et al., "Antimony Oxides : a Guide to Phase Changes During Catalyst Preparation", Applied Catalysis, vol. 48, pp. 123-135, 1989.

(Continued)

*Primary Examiner* — Colleen Dunn
*Assistant Examiner* — Haytham Soliman
(74) *Attorney, Agent, or Firm* — Drinker Biddle & Reath LLP

(57) ABSTRACT

The present invention relates to a multilayer catalyst for preparing phthalic anhydride which has a plurality of catalyst layers arranged in succession in the reaction tube, with the individual catalyst layers having alkali metal contents which decrease in the flow direction. The present invention further relates to a process for the oxidation of naphthalene or o-xylene/naphthalene mixtures over such a multilayer catalyst and the use of such multilayer catalysts for the oxidation of naphthalene or o-xylene/naphthalene mixtures to phthalic anhydride.

4 Claims, No Drawings

(56) References Cited

FOREIGN PATENT DOCUMENTS

| | | |
|---|---|---|
| DE | 19824532 A1 | 12/1999 |
| DE | 19839001 A1 | 3/2000 |
| EP | 286448 A2 | 10/1988 |
| EP | 522871 A1 | 1/1993 |
| EP | 539878 A2 | 5/1993 |
| EP | 0 744 214 A1 | 11/1996 |
| EP | 1082317 A1 | 3/2001 |
| EP | 1084115 A1 | 3/2001 |
| EP | 1091806 A1 | 4/2001 |
| EP | 1636161 A1 | 3/2006 |
| EP | 2009520 A1 | 12/2008 |
| WO | WO-2004103561 A1 | 12/2004 |
| WO | WO-2004103943 A1 | 12/2004 |
| WO | WO-2005/030388 A1 | 4/2005 |
| WO | WO-2006125468 A2 | 11/2006 |
| WO | WO-2007116018 A1 | 10/2007 |
| WO | WO-2007134849 A1 | 11/2007 |
| WO | WO-2010/136551 A2 | 12/2010 |
| WO | WO-2011/080051 A1 | 7/2011 |

OTHER PUBLICATIONS

U. A. Schubert et al., "Possible effects of site isolation in antimony oxide-modified vanadia/titania catalysts for selective oxidation of o-xylene", Topics in Catalysis, vol. 15, No. 2-4, pp. 195-200, 2001.

Christer Svensson, "Refinement of the Crystal Structure of Cubic Antimony Trioxide, Sb2O3", Aeta Cryst., vol. B31, pp. 2016-2018, 1975.

Howard E. Swanson et al., "Standard X-ray Diffraction Powder Patterns", National Bureau of Standards Circular 539, vol. 10, pp. 6-8, 1960.

International Search Report from companion PCT/EP2010/067432 of Nov. 15, 2010.

International Search Report from PCT/IB2011/053327 dated Jan. 5, 2012.

Anastasov, A. I., "Deactivation of an industrial V2O5-TiO2 catalyster for oxidation of o-xylene into phthalic anhydride," Chemical Engineering and Processing, 2003, vol. 42, pp. 449-460.

Bond, G. C., "What Limits the Selectivity Attainable in the Catalysed Oxidation of o-Xylene to Phthalic Anhydride?" J. Chem. Tech. Biotechnol., 1997, vol. 68, pp. 6-13.

Galantowicz, M., et al., "Effect of thermal deactivation of vanadium—titanium catalyst on o-xylene oxidation process yielding phthalic anhydride," Studies in Surface Science and Catalysis, 1994, vol. 88, pp. 591-596.

Garcin, et al., "Preparation of V2O5/TiO2 Eurocat oxide catalysts," *Catalysis Today* 20 (1994), pp. 7-10.

Grzybowska-Świerkosz, "Vanadia-titania catalysts for oxidation of o-xylene and other hydrocarbons," *Applied Catalysis A: General* 157 (1997), pp. 263-310.

International Search Report for PCT/IB2011/052831, Nov. 17, 2011.

MULTILAYER CATALYST FOR PREPARING PHTHALIC ANHYDRIDE AND PROCESS FOR PREPARING PHTHALIC ANHYDRIDE

CROSS-REFERENCE TO RELATED APPLICATIONS

This application claims benefit (under 35 USC 119(e)) of U.S. Provisional Application 61/359,832, filed Jun. 30, 2010.

BACKGROUND OF THE INVENTION

The present invention relates to a multilayer catalyst for preparing phthalic anhydride which has a plurality of catalyst layers arranged in succession in the reaction tube, with the individual catalyst layers having alkali metal contents which decrease in the flow direction. The present invention further relates to a process for the oxidation of naphthalene or o-xylene/naphthalene mixtures over such a multilayer catalyst and the use of such multilayer catalysts for the oxidation of naphthalene or o-xylene/naphthalene mixtures to phthalic anhydride.

Many carboxylic acids and/or carboxylic anhydrides are prepared industrially by catalytic gas-phase oxidation of hydrocarbons such as benzene, the xylenes, naphthalene, toluene or durene in fixed-bed reactors. In this way, it is possible to obtain, for example, benzoic acid, maleic anhydride, phthalic anhydride, isophthalic acid, terephthalic acid or pyromellitic anhydride. In general, a mixture of an oxygen-comprising gas and the starting material to be oxidized is passed through tubes in which a bed of a catalyst is present. To regulate the temperature, the tubes are surrounded by a heat transfer medium, for example a salt melt.

Catalysts which have been found to be suitable for these oxidation reactions are coated catalysts in which the catalytically active composition is applied in the form of a shell to an inert support material such as steatite. In general, titanium dioxide and vanadium pentoxide are used as catalytically active constituents of the catalytically active composition of these coated catalysts. Furthermore, small amounts of many other oxidic compounds which act as promoters to influence the activity and selectivity of the catalyst can be comprised in the catalytically active composition.

It has been found to be particularly advantageous to use different catalysts in the catalyst bed which differ in terms of their catalytic activity and/or the chemical properties of their active composition. When using two reaction zones, the catalyst preferably used in the first reaction zone, i.e. the reaction zone located nearest the inlet for the reaction gas, has a somewhat lower catalytic activity than the catalyst present in the second reaction zone, i.e. the reaction zone nearest the gas outlet. In general, the reaction is controlled by means of the temperatures set so that the major part of the aromatic hydrocarbon comprised in the reaction gas is reacted with maximum yield in the first zone. Preference is given to using three- to five-layer catalyst systems, in particular three- and four-layer catalyst systems.

The oxidation of o-xylene to phthalic anhydride (PAn) over vanadium oxide/titanium dioxide catalyst systems is usually carried out at air flows of about 4 standard $m^3/h$ and o-xylene loadings of up to 100 g/standard $m^3$. For the oxidation of o-xylene/naphthalene mixtures, the catalysts have typically been developed so that they are particularly well suited to a particular o-xylene/naphthalene mixing ratio or a narrow range of o-xylene/naphthalene mixing ratios. If the o-xylene/naphthalene ratio is altered significantly, either the PAn yield decreases drastically, the product quality becomes significantly poorer and/or the operative life of the catalyst is adversely affected. This is particularly pronounced at high loadings of o-xylene or naphthalene. The higher the total loading of o-xylene and naphthalene, the smaller the range of possible o-xylene/naphthalene ratios.

EP 539878 describes a process for the oxidation of o-xylene/naphthalene mixtures over a two-layer catalyst. Weight ratios of from 10/90 to 90/10% are used, and the maximum total loading in a single pass is 70 g/standard $m^3$ at a space velocity (GHSV) of 3000 $h^{-1}$. The PAn yields are in the range from 98.5 to 111.5% by weight, depending on the catalyst and o-xylene/naphthalene mixing ratio.

In EP 744214, PAn yields of only 101% by weight were achieved at a naphthalene loading of 80 g/standard $m^3$ and 4 standard $m^3/h$ of air.

In the case of a two-layer catalyst as described in EP 1082317, a PAn yield of 110% by weight was achieved at from 65 to 80 g/standard $m^3$ and a 75% by weight/25% by weight o-xylene/naphthalene mixture and 4 standard $m^3/h$ of air. Variation of the o-xylene/naphthalene ratio was not carried out.

The two-layer catalysts in EP 286448 were operated using 70 g/standard $m^3$ of naphthalene and a GHSV of 3000 $h^{-1}$. However, the o-xylene/naphthalene ratios were varied only from 100:0 to 50:50 or from 50:50 to 0:100 for individual catalysts. Wider variation of the mixing ratios using the same catalyst is not described.

Catalysts having more than two catalyst layers have been described for the oxidation of o-xylene to phthalic anhydride even at very high loadings of o-xylene of up to 100 g/standard $m^3$ at 4 standard $m^3/h$ of air. An example is a three-layer catalyst system for the oxidation of o-xylene to PAn as described in EP 1084115. However, these catalysts are not suitable for the oxidation of o-xylene/naphthalene mixtures at total loadings of at least 80 g/standard $m^3$ at about 4 standard $m^3/h$ of air with a wide variation of the o-xylene/naphthalene ratio.

There is a continuing need for catalysts for gas-phase oxidations which give a very high conversion at high selectivity.

BRIEF SUMMARY OF THE INVENTION

It was an object of the present invention to develop a catalyst for the oxidation of naphthalene or o-xylene/naphthalene mixtures at total loadings of at least 80 g/standard $m^3$ at about 4 standard $m^3/h$ of air, in which the o-xylene/naphthalene ratio can be varied over a very wide range at a high PAn yield and good product quality.

This object is achieved by a multilayer catalyst for the oxidation of naphthalene or o-xylene/naphthalene mixtures to phthalic anhydride, in which each catalyst layer comprises vanadium oxide and titanium dioxide and the alkali metal content of the catalyst layers decreases from layer to layer in the flow direction.

The invention accordingly provides a multilayer catalyst for the oxidation of naphthalene or o-xylene/naphthalene mixtures to phthalic anhydride, which comprises at least three catalyst layers which each comprise vanadium oxide and titanium dioxide and have alkali metal contents selected so that a) the alkali metal content of one catalyst layer A is the highest, b) a catalyst layer Z which follows the catalyst layer A in the flow direction has an alkali metal content of from 0 to 10% of the alkali metal content of the catalyst layer A and c) the catalyst layers located between the catalyst layers A and Z have an alkali metal content of from 30 to 90% of the alkali metal content of the catalyst layer A, with the alkali metal content of each catalyst layer being higher than the alkali metal content of the next catalyst layer in the flow direction.

DETAILED DESCRIPTION OF THE INVENTION

In a preferred embodiment of the invention, the multilayer catalyst has three, four or five layers. Particular preference is given to three- and four-layer catalysts.

The multilayer catalysts of the invention can, for example, be used for avoiding high hot spot temperatures, if appropriate in combination with suitable upstream and/or downstream beds and also together with intermediate layers, with the upstream and/or downstream beds and the intermediate layers generally being able to comprise catalytically inactive or less active material.

A further preferred embodiment of the invention is a four-layer catalyst for the oxidation of naphthalene or o-xylene/naphthalene mixtures to phthalic anhydride, in which each catalyst layer comprises vanadium oxide and titanium dioxide and the alkali metal contents of the catalyst layers are selected so that a) the alkali metal content of one catalyst layer A is the highest, b) a catalyst layer B which follows the catalyst layer A in the flow direction has an alkali metal content of from 60 to 90% of the alkali metal content of the catalyst layer A, c) a catalyst layer C which follows the catalyst layer B in the flow direction has an alkali metal content of from 30 to 59% of the alkali metal content of the catalyst layer A, d) a catalyst layer Z which follows the catalyst layer C in the flow direction has an alkali metal content of from 0 to 10% of the alkali metal content of the catalyst layer A.

The catalysts of the invention are generally coated catalysts in which the catalytically active composition is applied in the form of a shell to an inert support material.

As inert support material, it is possible to use virtually all support materials of the prior art as can advantageously be used in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The catalyst supports can be used, for example, in the form of spheres, rings, pellets, spirals, tubes, extrudates or crushed material. The dimensions of these catalyst supports correspond to the catalyst supports customarily used for the production of coated catalysts for the gas-phase reactions of aromatic hydrocarbons. Preference is given to using steatite in the form of spheres having a diameter of from 3 to 6 mm or of rings having an external diameter of from 5 to 9 mm and a length of from 3 to 8 mm and a wall thickness of from 1 to 2 mm.

The catalysts of the invention comprise a catalytically active composition which comprises at least vanadium oxide and titanium dioxide and can be applied in one or more layers to the support material. Various layers can differ in respect of their composition.

The catalytically active composition preferably comprises, based on the total amount of the catalytically active composition, from 1 to 40% by weight of vanadium oxide, calculated as $V_2O_5$, and from 60 to 99% by weight of titanium dioxide, calculated as $TiO_2$. In preferred embodiments, the catalytically active composition can further comprise up to 1% by weight of a cesium compound, calculated as Cs, up to 1% by weight of a phosphorus compound, calculated as P, and up to 10% by weight of antimony oxide, calculated as $Sb_2O_3$. All figures for the chemical makeup of the catalytically active composition are based on the calcined state of the latter, e.g. after calcination of the catalyst at 450° C. for one hour.

Titanium dioxide is usually used in the anatase form for the catalytically active composition. The titanium dioxide preferably has a BET surface area of from 15 to 60 $m^2/g$, in particular from 15 to 45 $m^2/g$, particularly preferably from 13 to 28 $m^2/g$. The titanium dioxide used can comprise a single titanium dioxide or a mixture of titanium dioxides. In the latter case, the value of the BET surface area is the weighted average of the contributions of the individual titanium dioxides. The titanium dioxide used advantageously comprises, for example, a mixture of a $TiO_2$ having a BET surface area of from 5 to 15 $m^2/g$ and a $TiO_2$ having a BET surface area of from 15 to 50 $m^2/g$.

Suitable vanadium sources are, in particular, vanadium pentoxide and ammonium metavanadate. Suitable antimony sources are various antimony oxides, in particular antimony trioxide. Vanadium and antimony can also be used in the form of a vanadium antimonate compound. The vanadium antimonate introduced into the active composition of at least one layer can be prepared by reacting any vanadium and antimony compounds. Preference is given to direct reaction of the oxides to form a mixed oxide or vanadium antimonate. The vanadium antimonate can have various molar ratios of vanadium to antimony and optionally also comprise further vanadium or antimony compounds and be used in admixture with further vanadium or antimony compounds.

Possible phosphorus sources are, in particular, phosphoric acid, phosphorous acid, hypophosphorous acid, ammonium phosphate or phosphoric esters and especially ammonium dihydrogenphosphate. Possible sources of cesium are the oxide or hydroxide or the salts which can be converted thermally into the oxide, e.g. carboxylates, in particular the acetate, malonate or oxalate, carbonate, hydrogencarbonate, sulfate or nitrate.

Apart from the optional additives cesium and phosphorus, small amounts of many other oxidic compounds which act as promoters to influence the activity and selectivity of the catalyst, for example by reducing or increasing its activity, can be comprised in the catalytically active composition. Examples of such promoters are the alkali metals, in particular the abovementioned cesium and also lithium, potassium and rubidium, which are usually used in the form of their oxides or hydroxides, thallium (I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide.

Among the promoters mentioned, preference is given to the oxides of niobium and tungsten as additives in amounts of from 0.01 to 0.50% by weight, based on the catalytically active composition.

The layer(s) of the coated catalyst is/are advantageously applied by spraying a suspension of $TiO_2$ and $V_2O_5$, which optionally comprises sources of the abovementioned promoter elements, onto the fluidized support. Before the coating operation, the suspension is preferably stirred for a sufficiently long time, e.g. from 2 to 30 hours, in particular from 12 to 25 hours, for agglomerates of the suspended solids to break up and for a homogeneous suspension to be obtained. The suspension typically has a solids content of from 20 to 50% by weight. The suspension medium is generally aqueous, e.g. water itself or an aqueous mixture with a water-miscible organic solvent, e.g. methanol, ethanol, isopropanol, formamide and the like.

In general, organic binders, preferably copolymers, advantageously in the form of an aqueous dispersion, of acrylic acid-maleic acid, vinyl acetate-vinyl laurate, vinyl acetate-acrylate, styrene-acrylate or vinyl acetate-ethylene, are added to the suspension. The binders are commercially available as aqueous dispersions having a solids content of, for example, from 35 to 65% by weight. The amount of such binder dispersions used is generally from 2 to 45% by weight, preferably from 5 to 35% by weight, particularly preferably from 7 to 20% by weight, based on the weight of the suspension.

The support is fluidized in an ascending gas stream, in particular air, in, for example, a fluidized-bed or moving-bed apparatus. The apparatuses usually comprise a conical or spherical vessel in which the fluidizing gas is introduced from the bottom or from above via an immersed tube. The suspension is sprayed into the fluidized bed via nozzles from above, from the side or from below. The use of a riser tube which is arranged centrally or concentrically around the immersed tube is advantageous. A relatively high gas velocity which transports the support particles upward prevails within the riser tube. In the outer ring, the gas velocity is only a little above the loosening velocity. The particles are in this way moved vertically in a circular fashion. A suitable fluidized-bed apparatus is described, for example, in DE-A 4006935.

When coating the catalyst support with the catalytically active composition, coating temperatures of from 20 to 500° C. are generally employed, with coating being able to be carried out under atmospheric pressure or under reduced pressure. In general, coating is carried out at from 0° C. to 200° C., preferably from 20 to 150° C., in particular from 60 to 120° C.

The layer thickness of the catalytically active composition is generally from 0.02 to 0.2 mm, preferably from 0.05 to 0.15 mm. The proportion of active composition in the catalyst is usually from 5 to 25% by weight, mostly from 7 to 15% by weight.

As a result of thermal treatment at temperatures of from >200 to 500° C. of the precatalyst obtained in this way, the binder is given off from the applied layer as a result of thermal decomposition and/or combustion. The thermal treatment is preferably carried out in situ in the gas-phase oxidation reactor.

Instead of delineated layers of the various catalysts, it is also possible to obtain a pseudocontinuous transition between the layers and thus an effectively uniform decrease in the alkali metal content by inserting a zone comprising a mixture of the successive catalysts at the transition from one layer to the next layer.

The bed length of catalyst layer A is preferably in the range from 10 to 50%, particularly preferably in the range from 15 to 30%, of the total catalyst fill height in the reactor. The bed height of the catalyst layers A and B or A, B and C is advantageously in the range from 60 to 95% of the total catalyst fill height. Typical reactors have a fill height of from 250 cm to 350 cm. The catalyst layers can, if desired, also be distributed over a plurality of reactors.

The catalysts of the invention are particularly suitable for the oxidation of naphthalene or o-xylene/naphthalene mixtures to phthalic anhydride at a total loading in the range from 80 to 100 g/standard $m^3$ and an air flow of about 4 standard $m^3$/h.

The invention further provides a process for the oxidation of naphthalene or o-xylene/naphthalene mixtures to phthalic anhydride using a multilayer catalyst comprising at least three catalyst layers which each comprise vanadium oxide and titanium dioxide and have alkali metal contents selected so that a) the alkali metal content of one catalyst layer A is the highest, b) a catalyst layer Z which follows the catalyst layer A in the flow direction has an alkali metal content of from 0 to 10% of the alkali metal content of the catalyst layer A and c) the catalyst layers located between the catalyst layers A and Z have an alkali metal content of from 30 to 90% of the alkali metal content of the catalyst layer A, with the alkali metal content of each catalyst layer being higher than the alkali metal content of the next catalyst layer in the flow direction.

A preferred embodiment of the invention is a process for the oxidation of naphthalene or o-xylene/naphthalene mixtures to phthalic anhydride using a four-layer catalyst in which each catalyst layer comprises vanadium oxide and titanium dioxide and the alkali metal contents of the catalyst layers are selected so that a) the alkali metal content of one catalyst layer A is the highest, b) a catalyst layer B which follows the catalyst layer A in the flow direction has an alkali metal content of from 60 to 90% of the alkali metal content of the catalyst layer A, c) a catalyst layer C which follows the catalyst layer B in the flow direction has an alkali metal content of from 30 to 59% of the alkali metal content of the catalyst layer A, d) a catalyst layer Z which follows the catalyst layer C in the flow direction has an alkali metal content of from 0 to 10% of the alkali metal content of the catalyst layer A.

The invention further provides for the use of a multilayer catalyst comprising at least three catalyst layers which each comprise vanadium oxide and titanium dioxide and have alkali metal contents selected so that a) the alkali metal content of one catalyst layer A is the highest, b) a catalyst layer Z which follows the catalyst layer A in the flow direction has an alkali metal content of from 0 to 10% of the alkali metal content of the catalyst layer A and c) the catalyst layers located between the catalyst layers A and Z have an alkali metal content of from 30 to 90% of the alkali metal content of the catalyst layer A, with the alkali metal content of each catalyst layer being higher than the alkali metal content of the next catalyst layer in the flow direction for the oxidation of naphthalene or o-xylene/naphthalene mixtures to phthalic anhydride.

A preferred embodiment of the invention is the use of a four-layer catalyst in which each catalyst layer comprises vanadium oxide and titanium dioxide and the alkali metal contents of the catalyst layers are selected so that a) the alkali metal content of one catalyst layer A is the highest, b) a catalyst layer B which follows the catalyst layer A in the flow direction has an alkali metal content of from 60 to 90% of the alkali metal content of the catalyst layer A, c) a catalyst layer C which follows the catalyst layer B in the flow direction has an alkali metal content of from 30 to 59% of the alkali metal content of the catalyst layer A, d) a catalyst layer Z which follows the catalyst layer C in the flow direction has an alkali metal content of from 0 to 10% of the alkali metal content of the catalyst layer A for the oxidation of naphthalene or o-xylene/naphthalene mixtures to phthalic anhydride.

EXAMPLES

Production of the First Catalyst Layer CL1

2000 g of steatite rings (magnesium silicate) having an external diameter of 8 mm, a length of 6 mm and wall thickness of 1.5 mm were sprayed at 90° C. with 900 g of a suspension of 662.8 g of anatase (Fuji TA 100° C., BET surface area: 20 m$^2$/g), 29.52 g of vanadium pentoxide, 78.48 g of oxalic acid, 0.62 g of potassium sulfate, 8.31 g of cesium sulfate, 1.39 g of niobium pentoxide, 0.79 g of ammonium dihydrogenphosphate, 212.9 g of formamide, 1000 g of water and 67.5 g of binder (copolymer of acrylic acid-maleic acid in a weight ratio of 75/25 as aqueous polymer solution having a solids content of 49.4% by weight; the preparation of the binder is described in EP 1091806) in a fluidized-bed coater. The catalytically active composition applied in this way comprised 0.03% by weight of phosphorus (calculated as P), 4.22% by weight of vanadium (calculated as $V_2O_5$), 0.87% by weight of cesium (calculated as Cs), 0.2% by weight of Nb (calculated as $Nb_2O_5$), 0.04% by weight of K (calculated as K) and 94.68% by weight of titanium dioxide. The content of active composition after calcination at 450° C. for 1 hour was 8.9%.

Production of the Second Catalyst Layer CL2

The catalyst was produced by varying the composition of the suspension compared to CL1. The catalytically active composition applied in this way comprised 0.03% by weight of phosphorus (calculated as P), 4.22% by weight of vanadium (calculated as $V_2O_5$), 0.67% by weight of cesium (calculated as Cs), 0.2% by weight of Nb (calculated as $Nb_2O_5$), 0.03% by weight of K (calculated as K) and 94.85% by weight of titanium dioxide. The content of active composition after calcination at 450° C. for 1 hour was 8.8%.

Production of the Third Catalyst Layer CL3

The catalyst was produced by varying the composition of the suspension compared to CL1. The catalytically active composition applied in this way comprised 0.03% by weight of phosphorus (calculated as P), 4.22% by weight of vanadium (calculated as $V_2O_5$), 0.45% by weight of cesium (calculated as Cs), 0.2% by weight of Nb (calculated as $Nb_2O_5$), 0.02% by weight of K (calculated as K) and 95.1% by weight of titanium dioxide. The content of active composition after calcination at 450° C. for 1 hour was 9.0%.

Production of the Fourth Catalyst Layer CL4

The catalyst was produced by varying the composition of the suspension compared to CL1. The catalytically active composition applied in this way comprised 0.02% by weight of phosphorus (calculated as P), 4.22% by weight of vanadium (calculated as $V_2O_5$), 0.00% by weight of cesium (calculated as Cs), 0.2% by weight of Nb (calculated as $Nb_2O_5$), 0.00% by weight of K (calculated as K) and 95.56% by weight of titanium dioxide. The content of active composition after calcination at 450° C. for 1 hour was 9.6%.

Description of the Oxidation of o-Xylene to Phthalic Anhydride

The catalytic oxidation of o-xylene to phthalic anhydride was carried out in a tube reactor which had an internal diameter of the tube of 25 mm and was cooled by means of a salt bath. To record temperature profiles, the reactor tube was equipped with a thermocouple. 4.0 standard m$^3$/h of air having an o-xylene (purity about 99% by weight) or naphthalene (purity about 97.5% by weight) loading of from 0 to 85 g/standard m$^3$ were passed through the tubes. The PAn yields were measured in the reactor exit gas and are reported in % by weight (kg of PAn per kg of o-xylene or naphthalene reacted) based on 100% pure o-xylene or 100% pure naphthalene.

Results and Examples

Example 1

According to the Invention

Bed length distribution: steatite preliminary bed/CL1/CL2/CL3/CL4 5 cm/80 cm/80 cm/90 cm/90 cm At a naphthalene loading of 80 g/standard m$^3$, 4 standard m$^3$/h of air and a salt bath temperature of 360° C., a PAn yield of 105.6% by weight and a phthalide and naphthoquinone content of 0.00 and 0.53% by weight, respectively, were achieved. For a 50:50 mixture of o-xylene and naphthalene at a total loading of 80 g/standard m$^3$, 4 standard m$^3$/h of air and a salt bath temperature of 362° C., a PAn yield of 110.1% by weight and a phthalide and naphthoquinone content of 0.06 and 0.41% by weight, respectively, were achieved. At a naphthalene loading of 30 g/standard m$^3$ and an o-xylene loading of 55 g/standard m$^3$ (total loading: 85 g/standard m$^3$), 4 standard m$^3$/h of air and a salt bath temperature of 362° C., a PAn yield of 111.0% by weight and a phthalide and naphthoquinone content of 0.11 and 0.34% by weight, respectively, were achieved. At a total loading of at least 80 g/standard m$^3$ at 4 standard m$^3$/h of air, the o-xylene/naphthalene ratio could thus be varied in the range from 0:100% to 65:35% while maintaining a high PAn yield and a good product spectrum (low yields of phthalide and naphthoquinone). The hot spot temperatures were below 450° C. for all feed compositions.

Example 2

Not According to the Invention

Bed length distribution: steatite preliminary bed/CL1/CL2/CL3/CL4 20 cm/100 cm/0 cm/90 cm/100 cm At a naphthalene loading of 80 g/standard m$^3$, 4 standard m$^3$/h of air and a salt bath temperature of 358° C., a PAn yield of 104.7% by weight and a phthalide and naphthoquinone content of 0.00 and 0.55% by weight, respectively, were achieved. For a 50:50 mixture of o-xylene and naphthalene at a total loading of 80 g/standard m$^3$, 4 standard m$^3$/h of air and a salt bath temperature of 364° C., a PAn yield of 109.6% by weight and a phthalide and naphthoquinone content of 0.03 and 0.31% by weight, respectively, were achieved. The hot spot temperatures were below 450° C. for all feed compositions. When the feed composition was changed further to a naphthalene loading of 30 g/standard m$^3$ and an o-xylene loading of 55 g/standard m$^3$ (total loading: 85 g/standard m$^3$), the hot spot temperatures rose to above 465° C. The catalyst could not be operated in a stable fashion at this feed composition. At a total loading of at least 80 g/standard m$^3$ at 4 standard m$^3$/h of air, the o-xylene/naphthalene ratio could thus be varied only in the range from 0:100% to 50:50% if a high PAn yield and a good product spectrum (low yields of phthalide and naphthoquinone) were to be obtained.

The invention claimed is:
1. A multilayer catalyst for the oxidation of naphthalene or o-xylene/naphthalene mixtures to phthalic anhydride, which comprises at least three catalyst layers which each comprise vanadium oxide and titanium dioxide and have alkali metal contents selected so that
   a) the alkali metal content of one catalyst layer A, which has a bed length in the range from 15 to 30% of the total catalyst fill height in the reactor, is the highest, b) a catalyst layer Z which follows the catalyst layer A in the flow direction has an alkali metal content of from 0 to 10% of the alkali metal content of the catalyst layer A and c) the catalyst layers located between the catalyst layers A and Z have an alkali metal content of from 30 to 90% of the alkali metal content of the catalyst layer A, with the alkali metal content of each catalyst layer being higher than the alkali metal content of the next catalyst layer in the flow direction and wherein at least one layer of said multilayer catalyst further comprises a promoter and said promoter is niobium oxide and the niobium oxide is present in an amount from 0.01 to 0.5% by weight, based on the catalytically active composition.

2. The multilayer catalyst according to claim 1 having four layers, wherein the alkali metal contents of the catalyst layers are selected so that a) the alkali metal content of one catalyst layer A, which has a bed length in the range from 15 to 30% of the total catalyst fill height in the reactor, is the highest, b) a catalyst layer B which follows the catalyst layer A in the flow direction has an alkali metal content of from 60 to 90% of the alkali metal content of the catalyst layer A, c) a catalyst layer C which follows the catalyst layer B in the flow direction has an alkali metal content of from 30 to 59% of the alkali metal content of the catalyst layer A, d) a catalyst layer Z which follows the catalyst layer C in the flow direction has an alkali metal content of from 0 to 10% of the alkali metal content of the catalyst layer A and wherein at least one layer of said multilayer catalyst further comprises a promoter and said promoter is niobium oxide and the niobium oxide is present in an amount from 0.01 to 0.5% by weight, based on the catalytically active composition.

3. The multilayer catalyst according to claim 2, wherein the bed height of the catalysts layers A, B, and C is in the range from 60 to 95% of the total catalyst fill height.

4. A process for the oxidation of naphthalene or o-xylene/naphthalene mixtures to phthalic anhydride which comprises utilizing the multilayer catalyst as claimed in claim 1.

\* \* \* \* \*